US010125169B2

(12) United States Patent
Forssmann et al.

(10) Patent No.: US 10,125,169 B2
(45) Date of Patent: Nov. 13, 2018

(54) PROTRANSDUZIN B, A GENE TRANSFER ENHANCER

(71) Applicant: Pharis Biotec GmbH, Hannover (DE)

(72) Inventors: Wolf-Georg Forssmann, Hannover (DE); Andreas Zgraja, Hannover (DE); Rudolf Richter, Hannover (DE)

(73) Assignee: Pharis Biotec GmbH, Hannover (DE)

(*) Notice: Subject to any disclaimer, the term of this patent is extended or adjusted under 35 U.S.C. 154(b) by 259 days.

(21) Appl. No.: 14/787,160

(22) PCT Filed: Apr. 30, 2014

(86) PCT No.: PCT/EP2014/058870
§ 371 (c)(1),
(2) Date: Oct. 26, 2015

(87) PCT Pub. No.: WO2014/177635
PCT Pub. Date: Nov. 6, 2014

(65) Prior Publication Data

US 2016/0185820 A1 Jun. 30, 2016

(30) Foreign Application Priority Data

May 2, 2013 (EP) .................................... 13166266

(51) Int. Cl.

| | |
|---|---|
| ***C07K 7/08*** | (2006.01) |
| ***C12N 15/87*** | (2006.01) |
| *A61K 38/00* | (2006.01) |
| *A61K 48/00* | (2006.01) |

(52) U.S. Cl.
CPC ................ *C07K 7/08* (2013.01); *C12N 15/87* (2013.01); *A61K 38/00* (2013.01); *A61K 48/00* (2013.01)

(58) Field of Classification Search
CPC ........................................................ C07K 7/08
See application file for complete search history.

(56) References Cited

U.S. PATENT DOCUMENTS

| | | | | |
|---|---|---|---|---|
| 8,652,483 B2 * | 2/2014 | Munch | C07K 14/005 424/184.1 |
| 2007/0123469 A1 * | 5/2007 | Larsen | C07K 5/06026 514/6.9 |
| 2012/0122177 A1 * | 5/2012 | Munch | C07K 14/005 435/174 |

FOREIGN PATENT DOCUMENTS

| | | | |
|---|---|---|---|
| EP | 2334318 | A2 | 6/2011 |
| EP | 2452947 | A1 | 5/2012 |
| JP | 2010537638 | A | 12/2010 |
| JP | 2013504519 | A | 2/2013 |
| WO | 2009032702 | A2 | 3/2009 |
| WO | 2011034207 | A1 | 3/2011 |
| WO | 2013033636 | A2 | 3/2013 |
| WO | 2013033636 | A3 | 3/2013 |

OTHER PUBLICATIONS

Kajiwara et al., 2009, Bioorganic synthesis of a recombinant HIV-1 fusion inhibitor, SC35EK, with an N-terminal pyroglutamate capping group, Bioorganic & Medicinal Chemistry, 17: 7964-7970.*
Burov et al., 2009, Incorporation of N-amidino-pyroglutamic acid into peptides using intramolecular cyclization of alpha-guanidinoglutaric acid, Journal of Peptide Science, 15(11): 760-766.*
Jawhar et al., "Pyroglutamate Amyloid-62 (AB): A Hatchet Man in Alzheimer Disease; Journal of Biological Chemistry", 286 (45):38825-38832 (2011).
Münch et al, "Peptide Nanofibrils Boost Retroviral Gene Transfer and Provide a Rapid Means for Concentrating Viruses", Nature Nanotechnology, 8:130-136 (Feb. 2013).
Wurm et al., "The Influence of Semen-Derived Enhancer of Virus Infection on the Efficiency of Retroviral Gene Transfer", Journal of Gene Medicine, 12:137-146 (2010).
Wurm et al., "Improved Lentiviral Gene Transfer Into Human Embryonic Stem Cells Grown in Co-Culture With Murine Feeder and Stroma Cells", Biology Chemical, 392:887-895 (2011).
Japanese Office Action of Application No. 2016-511064, Reference No. GNP-11103, Mailing No. 561970, dated Jan. 9, 2018. 5 pages.
Damen et al., "Delivery of DNA and SiRNA by Novel Gemini-Like Amphiphilic Peptides", Journal of Controlled Release 145, pp. 33-39, (2010).

* cited by examiner

*Primary Examiner* — Amber D Steele
(74) *Attorney, Agent, or Firm* — Christensen, Fonder, Dardi & Herbert PLLC; Curtis Herbert

(57) ABSTRACT

An N-terminally protected peptide having the sequence

```
                                       (SEQ ID NO: 1)
X-Glu-Cys-Lys-Ile-Lys-Gln-Ile-Ile-Asn-Met-Trp-Gln,
```

wherein X is a group protecting the N-terminal of the peptide.

8 Claims, 1 Drawing Sheet

Specification includes a Sequence Listing.

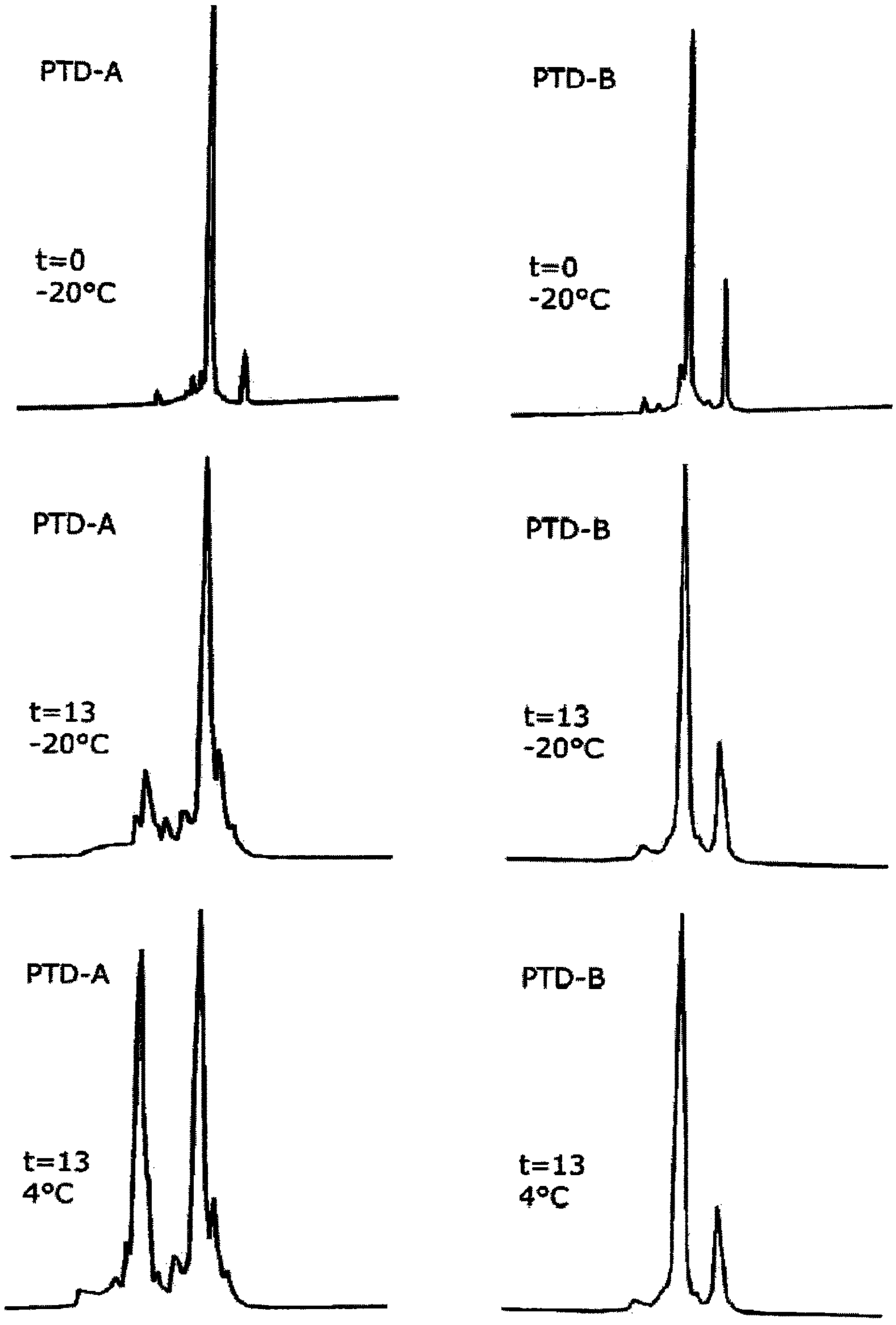
PTD-A
t=0
-20°C
PTD-B
t=0
-20°C
PTD-A
t=13
-20°C
PTD-B
t=13
-20°C
PTD-A
t=13
4°C
PTD-B
t=13
4°C

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial
<220> FEATURE:
<223> OTHER INFORMATION: Artificial N-terminal blocked Peptide

<400> SEQUENCE: 1

Glu Cys Lys Ile Lys Gln Ile Ile Asn Met Trp Gln
1               5                   10
```

PROTRANSDUZIN B, A GENE TRANSFER ENHANCER

CROSS REFERENCE TO RELATED APPLICATIONS

This application is a national stage filing of PCT Application No. PCT/EP2014/058870, filed Apr. 30, 2014, which claims priority to European Application No.: 13166266.0, filed May 2, 2013, all of which are incorporated herein by reference.

TECHNICAL FIELD OF THE INVENTION

The present application relates to an N-terminally protected peptide, to a medicament containing said peptide, to said peptide for use in gene therapy, to a method for enhancing the infection of a cell by a genetically engineered viral construct, and to the use of said peptide for amplification for transfection or transduction.

BACKGROUND

The importance of genetic engineering has increased in recent years because of an enormous progress in the applied methods, because it is predictable that not only the production of protein/peptide active substances, but also the transfection of cells with stable genes as a laboratory tool and ultimately the introduction of genes in cells as a remedy for gene defects will be highly relevant to the therapy of numerous diseases.

SUMMARY AND INTRODUCTION

The introduction of genetic material for changing specific cell functions has become an indispensable tool of biological-medical basic and applied research since the cloning of the first human genes and recombinant production, since the methods of gene transfer undergo continuous progress with increasing efficiency. Numerous methods of gene introduction have led to optimization. The corresponding experiences have been collected over many years of history, which was very slow at first.

BRIEF DESCRIPTION OF THE DRAWINGS

FIG. 1 is a high pressure liquid chromatography (HPLC) chromatogram of protransduzin A and protransduzin B.

Even before the elucidation of the function of deoxyribonucleic acid (DNA) in 1953 by F. Crick and J. Watson, F. Griffith had succeeded towards the end of the 1920's in experiments in transforming apathogenic *Pneumococcus* strains into pathogens. This transformation was due to a lucky circumstance, because the pneumococci had a rare natural competence of DNA uptake. A specific introduction of DNA into prokaryotes was achieved by J. Lederberg, M. Delbrück and S. Luria, among others, by means of phages, the so-called transduction. With the establishing of cell culture, the culturing of eukaryotic cells under in vitro conditions, a number of physical and chemical methods for transfection have been developed. The physical methods, which are more frequently utilized, but require more expensive equipment, include electroporation and microinjection, which competed with the more simply applicable chemical methods, such as the calcium phosphate precipitation method usual in the 1980's and still today, or the methods widespread in the early 1990's, which were based on cationic lipids or cationic polymers. However, the use of these methods has always been dependent on the cells or the DNA. Also, the DNA introduced into the cells was generally extrachromosomal (transient transfection), and thus it was not passed on to the daughter cells. However, phages (e.g., lambda phage) were known to be able to integrate their DNA into the host genome (prophage, lysogenic infection pathway). From here, it was only a small step (1981/1982) to the "Establishing of retroviruses as gene vectors" (by Doehmer et al. and Tabin et al.). Viruses are species-specific and organ/tissue-specific, which is why all viruses do not infect all (eukaryotic) cells. Alterations in the viral envelope (exchange of glycoproteins, so-called pseudotyped viruses) and additions of mostly cationic peptides are supposed to enhance transduction efficiency.

First enhancers of the uptake of virus particles attracted attention in the study of HIV. During analyses of in vitro infection by means of a specific cell test, the inhibition of the fusion of HIV by blood filtrate peptides was observed (Münch et al., VIRIP).

It has been shown that these fragments of proteins, which surprisingly are naturally occurring, form fibrous structures as enhancers in human sperm, "Semen derived Enhancer of Virus Infection" (SEVI), which are characterized as amyloid fibrils. These nanofibrils enhance the docking of viruses to their target cells, increasing the rate of viral infection by several powers of ten.

This was utilized for improving retroviral gene transfer for basic research and for possible future therapeutic applications. Thus, it could be shown that lentiviral and gammaretroviral viruses, which are used for gene therapy, exhibit a many times higher gene transfer rate in the presence of the SEVI protein for different cell types, such as human T cells, cervical carcinoma cells, leukemia cells, hematopoietic stem cells, and embryonic stem cells (Wurm et al., J. Gene Med. 2010, 12, 137-46; Wurm et al., Biol. Chem. 2011, 392, 887-95).

Studies for the development of further enhancers, such as SEVI and seminogelin, led to the assumption that peptides from viral envelope proteins may also be suitable as enhancers of transfection, which surprisingly was an unexpectedly great success (Maral Yolamanova, Nature Nanotechnology). Thus, it could be shown, for example, that HIVs preincubated with different concentrations (1-100 μg/ml) of protransduzin A (synonym: EF-C) exhibit an infection rate with reporter cells that is increased by several powers of ten. As the mechanism of action, it was assumed that EF-C forms fibrillary structures that are capable of binding and concentrating viruses and accordingly amplifying the entry of the viruses into the cell. In addition to the infection with viral particles, EF-C enhances the transduction of lentiviral and retroviral particles with high efficiency in a wide variety of human cell types (T cells, glial cells, fibroblasts, hematopoietic stem cells) applied in gene therapy (Jan Münch et al., Nature Nanotechnology, Vol. 8, No. 2, pp. 130-136). EP 2 452 947 A1 also relates to protransduzin A.

Because of the increasing importance of gene technology as set forth above, more effective enhancers of gene transfer are desirable. The object of the invention is to provide an improved enhancer of gene transfer.

Surprisingly, it has been found that an N-terminally protected peptide having the sequence (SEQ ID NO: 1)
X-Glu-Cys-Lys-Ile-Lys-Gln-Ile-Ile-Asn-Met-Trp-Gln, wherein X is a group protecting the N-terminal of the peptide, achieves the object of the invention. In particular, X represents one or two alkyl groups, such as methyl, ethyl, propyl or butyl groups, an acyl group, such as an acetyl or propionyl group, or the group X-Glu is the amino acid pyroglutamic acid:

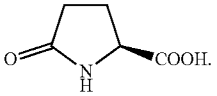

Surprisingly, it has been found that it is the modification of the N-terminal end by pyroglutamic acid in vitro (without cellular influences, especially the presence of enzymes), in particular, that results in an enormous increase in stability of the protransduzin in aqueous solution. This is clear from the results shown in FIG. 1.

In the left column of FIG. 1 (HPLC chromatogram), results for protransduzin A upon storage for 0-13 days at −20° C. and at 4° C. (13 days) are compared with the results for protransduzin B under the same conditions. It is clear that protransduzin A is degraded almost to one half upon storage at 4° C. for 13 days, whereas protransduzin B is hardly degraded at all under the same storage conditions (the height of the peaks corresponds to the concentration of the components contained in the sample).

In Journal of Biological Chemistry, Vol. 286, No. 45, pp. 38825-38832, S. Jawhar et al. report on the state of the science relating to amyloid peptides, especially pyroglutamate-modified amyloid polypeptides. Such amyloid polypeptides have a large number of amino acids and are basically not comparable to short-chained peptides, to which those according to the invention also belong. Incidentally, this mini review relates to cellular events occurring under in vivo conditions in the presence of enzymes, which is by no means comparable, however, to the conditions under which the stability of protransduzin has been improved according to the invention, i.e., in vitro conditions.

The peptide according to the invention may also be used as a medicament.

The invention also relates to the use of the peptide according to the invention in gene therapy for treating diseases that are treatable with gene therapy.

The invention also relates to a method for enhancing the infection of a cell by a virus, comprising the steps:

- providing the peptide according to claim 1 dissolved in an organic solvent;
- adding the peptide to an aqueous solution to form insoluble aggregates of the peptide;
- mixing the solution from the last preceding step; and
- culturing the cells.

The present invention also relates to the use of the peptide according to the invention for enhancing the infection of a cell with a virus.

Finally, a kit containing the peptide according to the invention is also claimed.

The peptide according to the invention (protransduzin B) can be prepared, for example, by the method according to Merrifield with Fmoc-protected amino acids.

This method works with Fmoc-protected derivatives, i.e., with (9-fluorenylmethoxycarbonyl)-protected amino acids, in a stepwise solid phase synthesis according to the Merrifield principle, especially on a Wang resin preloaded with Fmoc-L-glutamine (0.59 mmol/g, 100-200 mesh) as a solid support on the synthesizer ABI-433.

The activation of the Fmoc-L-amino acids, which were typically employed in a tenfold molar excess, is performed with [(2-(1H-benzotriazol-1-yl)-1,1,3,3-tetramethyluronium hexafluoro-phosphate] (HBTU, 100 mmol/l) with additions of 0.5 M 1-hydroxybenzotriazole (HOBt) and 2 M diisopropylethylamine (DIEA) in N-methyl-2-pyrrolidinone (NMP) at room temperature.

The individual acylation reactions take 45 minutes, and the Fmoc deprotection with 20% piperidine takes 15 minutes.

The following amino acid derivatives and related orthogonal acid-cleavable side chain protective groups are employed for synthesis:

Fmoc-L-Asn(Trt), Fmoc-L-Cys(Trt), L-pGlu, Fmoc-L-Gln (Trt), Fmoc-L-Ile, Fmoc-L-Lys(Boc), Fmoc-L-Met and Fmoc-L-Trp(Boc).

After cleaving the resin support from the peptidyl resin with 94% trifluoroacetic acid (TFA), 3% ethanedithiol (EDT) and 3% demineralized water, the raw peptide is precipitated in cold tert-butyl methyl ether, the raw peptide is centrifuged off as a pellet, and the supernatant is discarded.

The subsequent chromatographic purification of the raw peptide is effected in a preparative way by gradient elution.

The difference between protransduzin A according to EP 2 452 947 A1 and protransduzin B resides in the fact that the synthetic L-pyroglutamic acid (pGlu) is inserted N-terminally in exchange for synthetic L-glutamine (Gln) in protransduzin B. The original glutamine is modified by ring closure to form a lactam.

Purification:

Preparative separation: The purification is performed on an HPLC from the Gilson company. The UV/VIS detector is from the Kronwald company, and the separation is detected at the wavelength 230 nm. The flow rate is 40 ml/min.

The column is a Waters Prep-Pak C18 cartridge (47×300 mm).

Eluent A: 0.1% TFA in demineralized water; eluent B: 0.1% TFA in 80% acetonitrile and 20% demineralized water.

The gradient for protransduzin B is 35%-55% eluent B in 40 min, i.e., 0.5% eluent B per minute.

Protransduzin B elutes at 40% eluent B and is collected in several fractions of 0.5 to 1 min. The analytically clean fractions are pooled and lyophilized.

Processing for Application:

Lyophilization:

The unit Epsilon 1/45 of the Christ company, whose technical data are set as follows, is used for freeze drying: shelf area 3.78 $m^2$; ice capacity about 60 kg; ice condenser performance max. 45 kg/24 h; final partial pressure of vacuum pump $1\times10^{-3}/10^{-4}$ mbar with/without gas ballast; freeze-drying data (unit operated manually with gas ballast): final partial pressure $1\times10^{-2}$ mbar; ice condenser temperature −50° C.; shelf temperature +15° C.; operating point of shelf heating 0.5 mbar; freeze-drying time up to 3 days.

Transduction of Cells with Protransduzin B

Dissolve 0.5 mg of protransduzin B in 50 μl of DMSO. Then add 450 μl of PBS to the solution, fibrils forming within 3 min. Add this stock solution (1 mg/ml) to the vectors to obtain a concentration of protransduzin B of 25 μg/ml. Vortex the solution for 1 min, then centrifuge with 5000 g for 5 min. The supernatant is discarded, and the pellet is suspended in a little PBS and added to the cells. The cells are incubated in an incubator for 2 days.

The transduction rate is significantly enhanced by protransduzin B. Up to 96% of the cells can be transduced by means of protransduzin B.

The invention claimed is:

1. An N-terminally protected peptide of amino acids having the sequence of SEQ ID NO:1, wherein X-Glu protecting the N-terminal of the peptide is pyroglutamic acid.

2. The peptide according to claim 1 being an insoluble aggregate in an aqueous solution free of enzymes.

3. A medicament containing a peptide according to claim 1 being a solid or in a solution, with the medicament being free of enzymes.

4. A kit comprising a container containing a peptide according to claim 1.

5. The kit of claim 4 wherein
the peptide is dissolved in an organic solvent or
the peptide is a solid and the kit further comprises a liquid for mixing with the peptide.

6. A method of gene therapy, the method comprising exposing a cell to the peptide according to claim 1 and using the cell for gene therapy for treating diseases that are treatable with gene therapy.

7. A method for enhancing the infection of a cell by a virus, comprising the steps:
providing the peptide according to claim 1 dissolved in an organic solvent;
adding the peptide to an aqueous solution to form insoluble aggregates of the peptide;
mixing the solution from the last preceding step; and
culturing the cells.

8. A method for enhancing the infection of a cell by a virus comprising administering to a patient a peptide according to claim 1.

* * * * *